United States Patent [19]

Khare

[11] 4,038,378

[45] July 26, 1977

[54] RADIOIMMUNOASSAY FOR HEPATITIS B ANTIGEN

[76] Inventor: Gyaneshwar Prasad Khare, 311 S. Heatherstone St., Orange, Calif. 92669

[21] Appl. No.: 643,401

[22] Filed: Dec. 22, 1975

[51] Int. Cl.² ............................................. A61K 43/00
[52] U.S. Cl. ...................................... 424/1; 23/230 B
[58] Field of Search ........................... 424/1; 23/230 B

[56] References Cited

U.S. PATENT DOCUMENTS

| | | | |
|---|---|---|---|
| 3,794,467 | 2/1974 | Adams et al. | 23/230 B |
| 3,896,218 | 7/1975 | Charm et al. | 424/1 |

OTHER PUBLICATIONS

Catt et al., Nature, vol. 213, No. 5078, pp. 825–827, (Feb. 25, 1967).

*Primary Examiner*—Leland A. Sebastian

[57] ABSTRACT

The presence of hepatitis B antigen in serum or plasma can be detected by this technique. Commercially available imitation or cultured pearls coated with antibody to hepatitis B antigen are first reacted with the sample and subsequently reacted with radioactively labeled antibody to hepatitis B antigen. Hepatitis B antigen present in the sample forms a complex consisting of non-radioactive antibody-antigen-and radioactive antibody. The radioactivity emanating from these complexes on pearls is measured. This is indicative of the extent of binding of radioactive antibody and thereby indicating the presence or absence of hepatitis B antigen in an unknown sample.

8 Claims, No Drawings

RADIOIMMUNOASSAY FOR HEPATITIS B ANTIGEN

FIELD OF INVENTION

This discovery involves an improved methodology for detection of hepatitis B antigen in a human serum or plasma sample.

BACKGROUND OF THE INVENTION

Hepatitis B virus has been implicated to be the most probable etiologic agent for serum hepatitis or hepatitis of the long incubation variety. At least two distinct antigenic components have been found to be associated with hepatitis B virus. The first one, commonly known as hepatitis B surface antigen ($HB_sAg$) is present on the 20-nm spherical or filamentous form and 42-nm Dane particles. The other antigen designated as hepatitis B core antigen ($HB_cAg$) is found in the core of the 42-nm Dane particle. The antibodies for the two antigens are designated as anti-$HB_s$ and anti-$HB_c$ respectively. Blood or blood products containing hepatitis B virus can transmit Type B hepatitis following transfusion or parenteral inoculation. $HB_sAg$ circulates in the blood of patients actuely or chronically infected with hepatitis B virus. Since the original studies on the detection of $HB_sAg$ by immunodiffusion, several other methods have been developed for identification of this antigen. At present, radioimmunoassay for $HB_sAg$ appears to offer superior sensitivity than immunodiffusion, complement fixation, counterelectrophoresis and rheophoresis techniques. However, sensitivity of either of these methods for detection of hepatitis B surface antigen has been found to be a major problem in the elimination of post-transfusion, Type B hepatitis.

The radioimmunoassay technique (s) for hepatitis B surface antigen available at the time of invention wherein either the inside of a test tube is coated with anti-$HB_s$ derived from guinea pigs or beads or beadlets consisting of polystyrene or polythylene polymers are coated with anti-$HB_s$ derived from either guinea pigs or human patients. A serum or plasma sample containing hepatitis B antigen when added to the tube, an antigen-antibody complex is formed. When such complex is contacted with the radioactively labeled anti-$HB_s$, an additional complex is formed comprising a radioactive anti-$HB_s$; -$HB_sAg$;-non-radioactive anti-$HB_s$. Any non-complexed radioactive antibody is removed by subsequent washing of the tubes or beads or beadlets. The extent of radiation emitted by such complex is determined and compared with the known control and thereby the presence or absence of hepatitis B antigen is determined.

The object of present invention is to modify the entire methodology including the processes involved so as to achieve better sensitivity and specificity for Hepatitis B antigen (both $HB_sAg$ and $HB_cAg$), which would become more apparent in the following paragraphs.

DESCRIPTION OF THE PREFERRED EMBODIMENTS

According to the present invention, an improved process is provided in this solid phase radioimmunoassay for production of reagents or components to be used in the identification of hepatitis B antigen in human serum or plasma. One improvement lies in the choice of material used for coating the antibody. The solid phase radioimmunoassay described earlier has utilized the interior of a tube for antibody coating (Kevin Catt, et al., Journal of Biochemistry, Volume 100, pages 31c-33c, 1966 and Science. Volume 158, page 1570, 1967; C. M. Ling, U.S. Pat. No. 3,867,517). An improvement in this procedure is achieved by utilizing commercially available imitation or cultured pearls for antibody adsorption. Another improvement involves an art of coating the pearls with a solution containing anti-$HB_s$. The anti-$HB_s$ containing serum contains antibodies to two serotypes, ad and ay, of $HB_sAg$. Several methods are available to prepare antibody against $HB_sAg$ in animals. The antibody is preferably produced in goats following serial inoculations of $HB_sAg$ subtypes ad and/or ay. Commercially available pearls provide an excellent matrix for antibody attachment when used with a solution containing anti-$HB_s$. The usage of pearls not only facilitates absorption of anti-$HB_s$ present in the solution, but also increases the specificity and thereby providing efficient detection of $HB_sAg$ present in human serum or plasma. The size and the shape of these pearls could vary. However, spherical pearls of sizes ranging from 3 mm to about 8 mm are preferred. The number of pearls in one single reaction could also vary. However, one pearl of 6 mm size is preferred in a single reaction. These antibody coated pearls provide a solid matrix for this radioimmunoassay system.

The following examples will illustrate the details of the procedure.

EXAMPLE I

The pearls are coated by contacting them with a solution containing anti-$HB_s$. The solution consists of an aqueous buffer consisting of 0.02 M to about 0.08 M Tris (hydroxy methyl) aminomethane-HCl at pH from 7.4 to about 8.8; calcium chloride at a concentration from 0 to about 300 micrograms per ml and optimum levels of antibody containing anti-$HB_s$. A preservative, for example, sodium azide at concentrations from 400 micrograms to about 1,000 micrograms per ml may be added. The entire antibody solution is allowed to stand at 2° to about 8° C for zero to about 24 hours. The entire solution could be filter sterilized using a 0.2 micron sterile filter. A typical suitable buffer is 0.02 M Tris-HCl buffer at pH 7.4 containing 300 micrograms per ml of calcium chloride and optimum levels of anti-$HB_s$. The pearls are then coated with this solution. Approximately 17 ml ±0.5 ml of antibody solution is required for 100 pearls. The coating is achieved by incubating the pearls at 20° to about 37° C with the above mentioned solution within 16 hours. At the end of the coating period the solution is removed and the pearls are washed with Tris-HCl buffer (0.02 to about 0.08M, pH 7.4 to about 8.8) containing sodium azide at 400 micrograms per ml concentration. The remaining moisture content from the pearls is removed by lyophilization to a moisture content of less than 1%. The lyophilized pearls can be stored up to a period of six months at temperature of between −80° C to about 8° C.

EXAMPLE II $HB_sAg$ (ad and/or ay) is purified from human plasma or serum by ultracentrifugation. The procedure in brief entails centrifugation of plasma or serum at 35,000 rpm for three (3) hours and thereby collecting the resultant pellet. The pellet is suspended in 0.02 M of Tris-HCl buffer at pH 7.4. The suspended virus is centrifuged on a 1.1 to 1.4 g/ml of Cesium chloride gradient at 35,000 rpm for 18 hours. The centrifuged virus is collected and centrifuged again in Cesium chloride at a density of 1.20 grams/ml at 35,000 rpm for 24 hours. The resultant virus preparaton is resuspended in Cesium chloride at a density of 1.20 grams/ml and centrifuged again for 24 hours at 35,000 rpm. The virus so obtained is the purified preparation.

EXAMPLE III

Positive control in this technique consists of a heat inactivated $HB_sAg$ preparation at a concentration of 1.0 micrograms/ml in a suspending solution. This solution consists of 1 part of sterile recalcified human plasma (negative for antinuclear antibodies, rheumatoid factor, syphilis, anti-$HB_s$ and any contaminating $HB_sAg$) and 2 parts of the sterile 0.02 M Tris-HC1 buffer at pH 7.4 and sodium azide at a concentration of 1.0 milligrams/ml. The recalcified plasma is prepared by treating human plasma with 3.0% calcium chloride at a concentration of 1.0 ml of calcium chloride/30 ml of plasma. This entire mixture is incubated for 1 hour at 37° C and thereafter frozen at −20° C or lower. The contents are frozen and thawed 4 times, centrifuged and supernate filtered through a series of sterile filters ending through 0.2 micron filtration.

EXAMPLE IV

Negative control as used in this procedure is also a recalcified human plasma and is negative for antinuclear antibodies, rheumatiod factor, syphilis, anti-$HB_s$ and $HB_sAg$. Sodium azide at concentration 1.0 milligrams/ml may be added as a preservative.

EXAMPLE V

Antibody to hepatitis B surface antigen is labeled with a radioactive material. However, it is preferred to employ $^{125}I$ in the form of $Na^{125}I$. This procedure of producing a radioactively ($^{125}I$) labeled anti-$HB_s$ is identified here as iodination and is essentially a modification of Hunter and Greenwood (Nature, Volume 194, page 495, 1962). The radioactively labeled antibody to $HB_sAg$ is diluted to a final concentration of 0.4 to about 0.8 microcuries/ml using a radioactive antibody diluent. The diluent is prepared by diluting fetal calf serum 50:50 with Tris-HCl (0.02 M pH 7.4) and subsequently adding 10 ml of human serum (negative for antinuclear antibodies, rheumatoid factor, syphilis, anti-$HB_s$ and $HB_sAg$) to every 100 ml of diluted fetal calf serum. The diluent may be filter sterilized by filtering through 0.20 micron sterile filter. Sodium azide may be added as a preservative at a concentration of 1.0 milligrams/ml.

EXAMPLE VI

Serum or plasma may be assayed in this procedure. One pearl coated with anti-$HB_s$ is placed into a series of disposable tubes preferably glass. 0.2 ml of sample is placed in a tube. Likewise, negative control is added into six appropriately marked tubes and positive control in two appropriately marked tubes. The size of the tube or the volume of samples or controls are not important. However, it is preferred to use 0.2 ml of the controls or samples in 12 × 75 mm glass tubes, each containing individual pearls. The reaction time and temperature are variable but should be sufficient for an optimum antigen-antibody complex formation. Optimum reactivity is obtained at any time during the first 6 hours at 40° C.

At the end of the reaction, the entire reaction mixture is aspirated and the pearls are washed with water which may be distilled or deionized. The number of washings and the volume of wash solution are not important. Usually one wash with 2.0 to 3.0 ml of distilled or deionized water is sufficient.

Radioactive antibody to hepatits B surface antigen is subsequently added to each tube and the reaction continued for a time and temperature sufficient to form a non-radioactive antibody-antigen-radioactive antibody complex. Usually, 0.2 ml of radioactive antibody is added to each tube and the reaction is allowed to proceed for 1 hour at 40° C. The unreacted antibody is removed from each tube and the pearls washed again with distilled or deionized water to remove the remaining radioactive antibody. Usually two washings with 2.0 ml of wash solution are sufficient for this purpose, the only objective being to remove maximum proportions of unbound radioactive antibody without losing sensitivity or specficity. The amount of unbound radioactivity on each pearl is determined using a radioisotope counter capable of counting gamma radiation. In some instances the pearls may be transferred to clean glass or plastic tubes prior to counting to obtain better sensitivity. The extent of radiation emitted by the pearls from unknown sample or from positive control is compared by the extent of radiation emitted by the negative control treated pearls. The counts per minute (cpm) of unknown should be twice that of the average cpm of negative control for a $HB_sAg$ positive reaction. The positive control cpm should always be at least twice the average cpm of negative control.

This procedure is simple and requires less manipulation.

However, it is apparent that many alterations could be made in the procedures and product without departing from the scope and concept of the invention. The description presented herein should be interpreted as illustrative and not in a limiting sense.

I claim:

1. A process useful for the detection of hepatitis B antigen comprising
   a. Reacting an antibody to hepatits B antigen (anti-HB) coated pearl with human plasma or serum sample and allowing sufficient time for the antigen to forma complex with the antibody present on the pearl,
   b. Removing the sepcimen and washing the pearl with distilled or deionized water,
   c. Carrying on additional reaction following the addition of radioactively labeled antibody to form an additional complex on the pearl,
   d. Removing the non-associated radioactive antibody from the pearl and subsequently washing the pearl with distilled or deionized water to remove maximum proportions of unassociated radioactive antibody,
   e. Comparing the amount of radioactivity emanating from the sample treated pearls with that of negative control treated pearls.

2. A process as set forth in claim 1 wherein hepatitis B antigen refers either the hepatitis B surface antigen or to hepatitis B core antigen.

3. A process as set forth in claim 1 wherein the solid matrix described for use in the assay for hepatitis B antigen is a commercially available imitation or cultured pearl.

4. A process as described in claim 3 wherein the pearl is spherical.

5. A process as set forth in claim 1 wherein more than one spherical pearl could be used.

6. A process as set forth in claim 1 wherein the pearl is coated with antibody to hepatitis B antigen.

7. A process as in claim 6 wherein the antibody coating solution consists of an aqueous buffer consisting of 0.02 M to about 0.08 M Tris (hydroxy-methyl) aminomethane-HCl at pH 7.4 to about 8.8, calcium chloride at a concentration from 0 to about 300 micrograms/ml and optimum levels of antibody to hepatitis B antigen.

8. A process as set forth in claim 7 wherein antibody to hepatitis B antigen refers to the antibody to hepatitis B surface antigen which is a mixture of serotypes *a, d* and *y*, or antibody to heptatitis B core antigen.

* * * * *